United States Patent
Sambursky et al.

(10) Patent No.: US 9,910,036 B2
(45) Date of Patent: Mar. 6, 2018

(54) METHOD AND DEVICE FOR COMBINED DETECTION OF VIRAL AND BACTERIAL INFECTIONS

(75) Inventors: Robert P. Sambursky, Bradenton, FL (US); Uma Mahesh Babu, Bradenton, FL (US); Robert W. VanDine, Montoursville, PA (US)

(73) Assignee: RAPID PATHOGEN SCREENING, INC., Sarasota, FL (US)

( * ) Notice: Subject to any disclaimer, the term of this patent is extended or adjusted under 35 U.S.C. 154(b) by 544 days.

(21) Appl. No.: 12/782,162

(22) Filed: May 18, 2010

(65) Prior Publication Data

US 2010/0297611 A1 Nov. 25, 2010

Related U.S. Application Data

(63) Continuation-in-part of application No. 12/469,207, filed on May 20, 2009, now abandoned, which is a
(Continued)

(51) Int. Cl.
*G01N 33/558* (2006.01)
*G01N 33/543* (2006.01)
(Continued)

(52) U.S. Cl.
CPC ........ *G01N 33/54386* (2013.01); *B82Y 30/00* (2013.01); *G01N 33/54346* (2013.01);
(Continued)

(58) Field of Classification Search
CPC ....... G01N 33/56983; G01N 33/54346; G01N 33/36911; G01N 2333/4737; G01N 2333/914
(Continued)

(56) References Cited

U.S. PATENT DOCUMENTS 5,559,041 A  9/1996  Kang
5,569,608 A  10/1996  Sommer
(Continued)

FOREIGN PATENT DOCUMENTS

DE  4439429 C2  2/1996
DE  19622503 C2  7/1998
(Continued)

OTHER PUBLICATIONS

Uchio, et al., "Rapid Diagnosis of Adenoviral Conjunctivitis on Conjunctival Swabs by 10-Minute Immunochromatography," Opthalmology, vol. 104, No. 8, Aug. 1997, pp. 1294-1299.
(Continued)

*Primary Examiner* — Erik B Crawford
(74) *Attorney, Agent, or Firm* — Brown & Michaels, PC

(57) ABSTRACT

A lateral flow assay detects and differentiates between viral and bacterial infections. A combined point of care diagnostic device tests markers for viral infection and markers for bacterial infection, to effectively assist in the rapid differentiation of viral and bacterial infections. In one preferred embodiment, the bacterial marker is CRP. In another preferred embodiment, the viral marker is MxA. In some embodiments, it is unnecessary to lyse the cells in the sample prior to applying it to the device.

17 Claims, 6 Drawing Sheets

Related U.S. Application Data continuation-in-part of application No. 12/481,631, filed on Jun. 10, 2009, now Pat. No. 8,470,608, application No. 12/782,162, filed on May 18, 2010, which is a continuation-in-part of application No. 12/502,626, filed on Jul. 14, 2009, now Pat. No. 8,669,052, application No. 12/782,162, filed on May 18, 2010, which is a continuation-in-part of application No. 12/502,662, filed on Jul. 14, 2009, now Pat. No. 8,614,101, application No. 12/782,162, filed on May 18, 2010, which is a continuation-in-part of application No. PCT/US2009/057775, filed on Sep. 22, 2009.

(60) Provisional application No. 61/179,059, filed on May 18, 2009, provisional application No. 61/071,833, filed on May 20, 2008, provisional application No. 61/060,258, filed on Jun. 10, 2008, provisional application No. 61/080,879, filed on Jul. 15, 2008, provisional application No. 61/098,935, filed on Sep. 22, 2008.

(51) Int. Cl.
 *B82Y 30/00* (2011.01)
 *G01N 33/569* (2006.01)

(52) U.S. Cl.
 CPC . *G01N 33/56911* (2013.01); *G01N 33/56983* (2013.01); *B01J 2219/0074* (2013.01); *B01J 2219/00576* (2013.01); *B01J 2219/00648* (2013.01); *B01J 2219/00725* (2013.01); *B01J 2219/00743* (2013.01); *G01N 2333/47* (2013.01); *G01N 2333/4737* (2013.01); *G01N 2333/914* (2013.01)

(58) Field of Classification Search
 USPC ...... 435/5, 7.1, 7.2, 7.9–7.95; 436/810, 514, 436/518, 524–532, 536–541
 See application file for complete search history.

(56) References Cited

U.S. PATENT DOCUMENTS

| | | | |
|---|---|---|---|
| 6,106,779 A * | 8/2000 | Buechler | G01N 33/50 422/122 |
| 6,514,773 B1 | 2/2003 | Klein et al. | |
| 6,565,808 B2 | 5/2003 | Hudak et al. | |
| 6,727,073 B1 | 4/2004 | Moore et al. | |
| 7,189,522 B2 | 3/2007 | Esfandiari | |
| 7,267,992 B2 * | 9/2007 | Goerlach-Graw et al. | 436/514 |
| 7,379,167 B2 | 5/2008 | Mawhirt et al. | |
| 7,419,796 B2 | 9/2008 | Durst et al. | |
| 7,723,124 B2 | 5/2010 | Aberl et al. | |
| 2003/0027866 A1 * | 2/2003 | Johnson et al. | 514/564 |
| 2003/0119209 A1 * | 6/2003 | Kaylor et al. | 436/548 |
| 2004/0110167 A1 | 6/2004 | Gerdes et al. | |
| 2004/0203086 A1 * | 10/2004 | Piasio et al. | 435/11 |
| 2005/0130120 A1 * | 6/2005 | Lambotte et al. | 435/4 |
| 2005/0175992 A1 | 8/2005 | Aberl et al. | |
| 2005/0221386 A1 | 10/2005 | Turner et al. | |
| 2005/0227223 A1 | 10/2005 | Miyawaki | |
| 2005/0272106 A1 | 12/2005 | Moore et al. | |
| 2006/0121626 A1 | 6/2006 | Imrich | |
| 2006/0148097 A1 | 7/2006 | Yamaguchi et al. | |
| 2007/0003992 A1 | 1/2007 | Pentyala | |
| 2007/0059682 A1 | 3/2007 | Aberl et al. | |
| 2007/0141564 A1 | 6/2007 | Aberl et al. | |
| 2007/0184506 A1 | 8/2007 | Klepp | |
| 2007/0224701 A1 | 9/2007 | Rosenstein | |
| 2007/0264629 A1 | 11/2007 | Holmes et al. | |
| 2008/0057493 A1 | 3/2008 | Gao et al. | |
| 2008/0199851 A1 | 8/2008 | Egan et al. | |
| 2008/0310998 A1 | 12/2008 | Lamotte | |
| 2010/0143891 A1 | 6/2010 | Aberl et al. | |
| 2011/0151584 A1 | 6/2011 | Esfandiari | |

FOREIGN PATENT DOCUMENTS

| | | |
|---|---|---|
| DE | 10054093 A1 | 5/2002 |
| EP | 1489416 A1 | 12/2004 |
| EP | 1686378 A2 | 8/2006 |
| JP | 2006189317 A | 7/2006 |
| JP | 2007322310 A | 12/2007 |
| JP | 2008-537145 A | 9/2008 |
| WO | 0136975 A1 | 5/2001 |
| WO | 03073817 A2 | 9/2003 |
| WO | 2006115866 A1 | 11/2006 |
| WO | 2007063326 A2 | 6/2007 |
| WO | 2007081330 A1 | 7/2007 |
| WO | 2009108224 A1 | 9/2009 |

OTHER PUBLICATIONS

"Rapid test for pink eye may curb overuse of antibiotics", http://www.stjohns.com/news/pinkeyetest.aspx (Jan. 26, 2009).

Sambursky et al., "The RPS Adeno Detector for Diagnosing Adenoviral Conjunctivitis", Ophthalmology, vol. 113, No. 10, pp. 1758-1764 (Oct. 2006).

Sambursky, "510-K Summary of Safety and Effectiveness" (Sep. 14, 2005).

Udeh et al., "Cost Effectiveness of a Point-of-Care Test for Adenoviral Conjunctivitis", The American Journal of the Medical Sciences, vol. 336, No. 3, pp. 254-264 (Sep. 2008).

Chi H, Chin NC, Li WC, Huang FY, "Etiology of acute pharyngitis in children: is antibiotic therapy needed?", J Microbial Immunol Infect 2003;36(1): 26-30.

Ewig, S., and A. Torres, "Severe community-acquired pneumonia", Curr. Opin. Crit. Care. 2002; 8:453-460.

Restrepo, MI., JH Jorgensen, EM Mortensen, Anzueto A, "Severe community-acquired pneumonia: current outcomes, epidemiology, etiology, and therapy", Curr. Opin. Infect. Dis. 2001;14:703-709.

Jennings LC, Anderson TP, Beynon KA, et al., "Incidence and characteristics of viral community-acquired pneumonia in adults" 1Thorax 2008;63:42-48.

Verheij TJM, Salome PL, Bindels PJ, et al., "NHGStandaard Acuut hoesten. [Dutch College of General Practitioners Guidelines on Acute Cough]", Huisarts Wet 2003;46(9):496-506. (Original reference in Dutch together with English machine translation.).

Steinman MA, Gonzales R, Linder JA, Landefeld CS, "Changing Use of Antibiotics in Community-Based Outpatient Practice, 1991-1999", Ann Intern Med 2003, 138(7):525-533.

Van Duijn HJ, Kuyvenhoven MM, Schellevis FG, Verheij TJM, "Determinants of prescribing of second-choice antibiotics for upper and lower respiratory tract episodes in Dutch general practice", J Antimicrob Chemother 2005;56 (2):420-422.

Smith SM, Fahey T, Smucny J, Becker LA, "Antibiotics for acute bronchitis", Cochrane Database Syst Rev 2004, Issue 4.

Barden LS, Dowell SF, Schwartz B, Lackey C. "Current attitudes regarding use of antimicrobial agents", Clin Pediatr. 1998; 37:665-672.

Haller 0, Kochs G, "Interferon induced Mx proteins: Dynamin like GTPases with antiviral activity", Traffic. 2002; 3:710-717.

Makela MJ, Puhakka T, Ruuskanen 0, Leinonen M, Saikku P, Kimpimaki M, Blomqvist S, Hyypia T, Arstila P, "Viruses and bacteria in the etiology of the common cold", J Clin Microbiol. 1998;36:539 542.

Huang N, Morlock L, Lee CH, Chen LS, Chou YJ, "Antibiotic prescribing for children with nasopharyngitis (common colds), upper respiratory infections, and bronchitis who have health-professional parents", Pediatrics. 2005;116:826-832.

Baker MD, Bell LM, Avner JR, "Outpatient management without antibiotics of fever in selected infants", N. Engl J Med. 1993;329:1437-1441.

(56) References Cited

OTHER PUBLICATIONS

Baskin MN, O'Rourke EJ, Fleisher GR, "Outpatient treatment of febrile infants 28 to 89 days of age with intramuscular administration of ceftriaxone", J Pediatr. 1992;120:22-27.
Jaskiewicz JA, McCarthy CA, Richardson AC, White KC, Fisher DJ, Powell KR, Dagan R, and Febrile Infant Collaborative Study Group, "Febrile infants at low risk for serious bacterial infection—an appraisal of the Rochester criteria and implications for management", Pediatrics. 1994;94: 390-396.
Le Bon A, Tough DF, "Links between innate and adaptive immunity via type I interferon", Curr Opin Immunol. 2002; 14: 432-436.
Van der Bliek AM, "Functional diversity in the dynamin family", Trends Cell Biol. 1999;9:96-102.
Staeheli P, Haller 0, Boll W, Lindemann J, Weissmann C, "Mx protein: constitutive expression in 3T3 cells transformed with cloned Mx cDNA confers selective resistance to influenza virus", Cell. 1986;44:147-158.
Ronni T, Melen K, Malygin A, Julkunen I, 1993, "Control of IFN-inducible MxA gene expression in human cells", J Immunol 150:1715-1726.
Ronni T, Matikainen S, Sareneva T, Melen K, Pirhonen J, Keskinen P, Julkunen I, "Regulation of IFB-alpha/beta, MxA, 2',5'-oligoadenylate synthetase, and HLA gene expression in influenza A-infected human lung epithelial cells", J Immunol. 1997;158:2363-2374.
Itazawa T, Adachi Y, Imamura H, Okabe Y, Yamamoto J, Onoue Y, Adachi YS, Miyawaki T, Murakami G, "Increased lymphoid MxA expression in acute asthma exacerbation in children", Allergy. 2001;56:895-898.
Itazawa T, Adachi Y, Nakabayashi M, Fuchizawa T, Murakami G, Miyawaki T, "Theophylline metabolism in acute asthma with MxA-indicated viral infection", Pediatr Int. 2006;48:54-57.
Forster J, Schweizer M, Schumacher RF, Kaufmehl K, Lob S, "MxA protein in infants and children with respiratory tract infection", Acta Paediatr. 1996;85:163-167.
Halminen M, Ilonen J, Julkunen I, Ruuskanen 0, Simell 0, Makela MJ, "Expression of MxA protein in blood lymphocytes discriminates between viral and bacterial infections in febrile children", Pediatr Res. 1997; 41:647-650.
Chieux V, Hober D, Harvey J, Lion G, Lucidarme D, Forzy G, Duhamel M, Cousin J, Ducoulombier H, Wattre P, "The MxA protein levels in whole blood lysates of patients with various viral infections", J Virol Methods. 1998;70:183-191.
Chieux V, Hober D, Chehadeh W, Harvey J, Alm G, Cousin J, Ducoulombier H, Wattre P, "MxA protein in capillary blood of children with viral infections", J Med Virol. 1999;59:547-551.
Nakabayashi M, Adachi Y, Itazawa T, Okabe Y, Kanegane H, Kawamura M, Tomita A, Miyawaki T, "MxA-based recognition of viral illness in febrile children by a whole blood assay", Pediatr Res. 2006;60:770-4.
Simon A, Fah J, Haller 0, Staeheli P, "Interferon-regulated Mx genes are not responsive to interleukin-1, tumor necrosis factor, and other cytokines", J Virol. 1991;65:968-971.
Girardin E, Grau GE, Dayer JM, Roux-Lombard P, Lambert PH, "Tumor necrosis factor and interleukin-1 in the serum of children with severe infectious purpura", N Engl J Med. 1988;319:397-400.
Calandra T, Baumgartner JD, Grau GE, Wu MM, Lambert PH, Schellekens J, Verhoef J, Glauser MP, "Prognostic values of tumor necrosis factor/cachectin, interleukin-1, interferon-alpha, and interferon-gamma in the serum of patients with septic shock", Swiss-Dutch J5 Immunoglobulin Study Group, J. Infect Dis 1990;161:982-987.
McCarthy PL, Frank AL, Ablow RC, Masters SJ, Dolan TF, "Value of C-reactive protein test in the differentiation of bacterial and viral pneumonia", J Pediatr 1978;92:454-6.
Stuart J, Lewis SM. Monitoring the acute phase response [Editorial]. BMJ 1988;297:1143-4.
Young B, Gleeson M, Cripps AW, "C-reactive protein: a critical review", Pathology 1991;23:118-24.
Thompson D, Milford Ward A, Whicher H, "The value of acute phase protein measurements in clinical practice", Ann Clin Biochem 1992;29:123-31.
Diederichsen HZ, Skamling M, Diederichsen A, Grinsted P, Antonsen S, Petersen PH, Munck AP, Kragstrup J, "Randomised controlled trial of CRP rapid test as a guide to treatment of respiratory infections in general practice", Scand J Prim Health Care 2000, 18(1):39-43.
Dahler Eriksen BS, Lauritzen T, Lassen JF, Lund ED, Brandslund I, "Near-patient test for C-reactive protein in general practice: assessment of clinical, organizational, and economic outcomes", Clin Chem 1999, 45(4):478-485.
Hansson LO, Carlsson I, Hansson E, Hovelius B, Svensson P, Tryding N, "Measurement of C-reactive protein and the erythrocyte sedimentation rate in general practice", Scand J Prim Health Care 1995;13:39-45.
Hjortdahl P, Melbye H, "Does near-to-patient testing contribute to the diagnosis of streptococcal haryngitis in adults?", Scand J Prim Health Care 1994;12:70-6.
Lindback S, Hellgren U, Julander I, Hansson LO, "The value of C-reactive protein as a marker of bacterial infection in patients with septicaemia/endocarditis and influenza", Scand J Infect Dis 1989;21:543-9.
Melbye H, Straume B, Aasebo U, Brox J, "The diagnosis of adult pneumonia in general practice. The diagnostic value of history, physical examination and some blood tests", Scand J Prim Health Care 1988;6:111-7.
Djavani et al., "Early Blood Profiles of Virus Infection in a Monkey Model for Lassa Fever", Journal of Virology, Aug. 2007, p. 7960-7973, vol. 81, No. 15.
Leung et al., "InfectCheck CRP barcode-style lateral flow assay for semi-quantitative detection of C-reactive protein in distinguishing between bacterial and viral infections", Journal of Immunological Methods, 336 (2008), pp. 30-36.
Extended European Search Report, European Patent Office, dated Feb. 9, 2012, for Application EP 09 81 5363.
Pitossi et al., "A Functional GTP-Binding Motif Is Necessary for Antiviral Activity of Mx Proteins", Journal of Virology, Nov. 1993, vol. 67(11), pp. 6726-6732.
Muller-Doblies et al., "Innate Immune Responses of Calves during Transient Infection with a Noncytopathic Strain of Bovine Viral Diarrhea Virus", Clinical and Diagnostic Laboratory Immunology, Mar. 2004, vol. 11(2), p. 302-312.

* cited by examiner

METHOD AND DEVICE FOR COMBINED DETECTION OF VIRAL AND BACTERIAL INFECTIONS

REFERENCE TO RELATED APPLICATIONS

This application claims one or more inventions which were disclosed in Provisional Application No. 61/179,059, filed May 18, 2009, entitled "METHOD AND DEVICE FOR COMBINED DETECTION OF VIRAL AND BACTERIAL INFECTIONS". The benefit under 35 USC § 119(e) of the United States provisional application is hereby claimed, and the aforementioned application is hereby incorporated herein by reference.

This application is also a continuation-in-part application of application Ser. No. 12/469,207, filed May 20, 2009, entitled "NANOPARTICLES IN DIAGNOSTIC TESTS", which claimed priority from Provisional Application No. 61/071,833, filed May 20, 2008, entitled "NANOPARTICLES IN DIAGNOSTIC TESTS", application Ser. No. 12/481,631, filed Jun. 10, 2009, entitled "COMBINED VISUAL/FLUORESCENCE ANALYTE DETECTION TEST", which claimed priority from Provisional Application No. 61/060,258, filed Jun. 10, 2008, entitled "COMBINED VISUAL/FLUORESCENCE ANALYTE DETECTION TEST", application Ser. No. 12/502,626, filed Jul. 14, 2009, entitled "LATERAL FLOW NUCLEIC ACID DETECTOR", which claimed priority from Provisional Application No. 61/080,879, filed Jul. 15, 2008, entitled "LATERAL FLOW NUCLEIC ACID DETECTOR" and application Ser. No. 12/502,662, filed Jul. 14, 2009, entitled "IN SITU LYSIS OF CELLS IN LATERAL FLOW IMMUNOASSAYS", which claimed priority from Provisional Application No. 61/098,935, filed Sep. 22, 2008, entitled "IN SITU LYSIS OF CELLS IN LATERAL FLOW IMMUNOASSAYS" and PCT application Serial Number PCT/US2009/057775, filed Sep. 22, 2009, entitled "METHOD AND DEVICE FOR COMBINED DETECTION OF VIRAL AND BACTERIAL INFECTIONS". The aforementioned applications are hereby incorporated herein by reference.

BACKGROUND OF THE INVENTION

Field of the Invention

The invention pertains to the field of lateral flow immunoassays. More particularly, the invention pertains to a lateral flow immunoassay that rapidly detects viral and bacterial infection.

Description of Related Art

Fever is a common cause of childhood visits to urgent care centers for both family practice and pediatric offices. Most commonly, this relates to either a respiratory infection or gastroenteritis. The high incidence of fever in children and the precautious administration of unnecessary antibiotics is reason to develop a rapid screening test for the biomarkers that indicate viral and/or bacterial infection.

It is often challenging to differentiate viral from bacterial infections. This is especially true in young children that cannot verbalize their symptoms and in the outpatient setting where access to laboratory diagnostics is expensive, time consuming, and requires several days to produce a result. More recently, many new diagnostic markers have been identified. Several of these markers show great promise to differentiate viral from bacterial infections. Two such proteins include MxA and C-Reactive Protein (CRP). Most respiratory infections are related to pharyngitis of which 40% are caused by viruses and 25-50% by group A beta hemolytic streptococcus. The lesser causes are acute bronchiolitis and pneumonia.

Severe community-acquired pneumonia is caused by bacterial infections in around 60% of cases, requiring admission to an intensive care unit (ICU) for about 10% of patients. The remaining 30% are related to respiratory viruses.

About 80% of all antimicrobials are prescribed in primary care, and up to 80% of these are for respiratory tract indications. Respiratory tract infections are by far the most common cause of cough in primary care. Broad spectrum antibiotics are often prescribed for cough, including acute bronchitis, and many of these prescriptions will benefit patients only marginally if at all, and may cause side effects and promote antibiotic resistance. Factors that urge physicians to give antibiotics include the absence of an adequate diagnostic marker of bacterial infections, the concern about lack of patient follow-up, and the time pressure.

Mx proteins are members of the superfamily of high molecular weight GTPases. Accordingly, these GTPases are upregulated by type I alpha/beta or type II interferons (IFN). The Mx GTPases are expressed exclusively in IFN alpha/beta but not IFN gamma treated cells. Type I interferons play important roles in innate immune responses and have immunomodulatory, antiproliferative, and antiviral functions. Human MxA, a 78 kDa protein, accumulates in the cytoplasm of IFN treated cells and inhibits the replication of a wide range of viruses. MxA protein may offer certain advantages as a marker for viral infection over the other induced proteins such as 2', 5'-oligoadenylate synthetase, because of its lower basal concentration, longer half-life (2.3 days) and fast induction. MxA mRNA is detectable in isolated peripheral blood white blood cells stimulated with IFN within 1 to 2 h of IFN induction, and MxA protein begins to accumulate shortly thereafter.

Studies have shown that MxA protein expression in peripheral blood is a sensitive and specific marker for viral infection. The higher MxA levels in the viral infection group compared with the bacterial infection group can be explained by the fact that the MxA protein is induced exclusively by type I IFN and not by IFN-gamma, IL-1, TNF-alpha, or any of the other cyotokines by bacterial infection. Serum type I IFN levels remain within normal limits, even in patients with severe bacterial infections.

Similarly, most viral infections have been reported to cause little acute phase response, and low C-Reactive Protein (CRP) concentrations have been used to distinguish illnesses of viral origin from those of bacterial etiology. Because the plasma concentration of CRP increases rapidly after stimulation and decreases rapidly with a short half-life, CRP can be a very useful tool in diagnosing and monitoring infections and inflammatory diseases. In Scandinavia, point of care CRP testing is part of the routine evaluation of patients with respiratory infections in general practice, and its use has proved cost-effective. In general practice, CRP is found valuable in the diagnosis of bacterial diseases and in the differentiation between bacterial and viral infections. Often the diagnostic value of CRP is found superior to that of the erythrocyte sedimentation rate (ESR) and superior or equal to that of the white blood cell count (WBC).

Clinically, it can be challenging to differentiate certain systemic viral and bacterial infections. Bacterial cultures are usually performed in cases of severe infection such as pneumonia, or when the consequence of missing a diagnosis can lead to severe complications, such as with Strep throat. Often times, cultures are difficult to obtain. Unfortunately, viral cultures are not routinely performed due to the significant time delay in receiving results. New viral screening PCR panels are useful but they are expensive and do not provide information at the point of care. Thus, there remains a need for a simple, easy to use diagnostic test that is capable of differentiating viral and bacterial infections.

SUMMARY OF THE INVENTION

The present invention provides a lateral flow assay that is capable of detecting and differentiating viral and bacterial infections. A combined point of care diagnostic device tests markers for viral infection and markers for bacterial infection, to effectively assist in the rapid differentiation of viral and bacterial infections. In one preferred embodiment, the bacterial marker is CRP. In another preferred embodiment, the viral marker is MxA. In some embodiments of the invention, it is unnecessary to lyse the cells in the sample prior to applying it to the device.

DETAILED DESCRIPTION OF THE INVENTION

Figure 1:
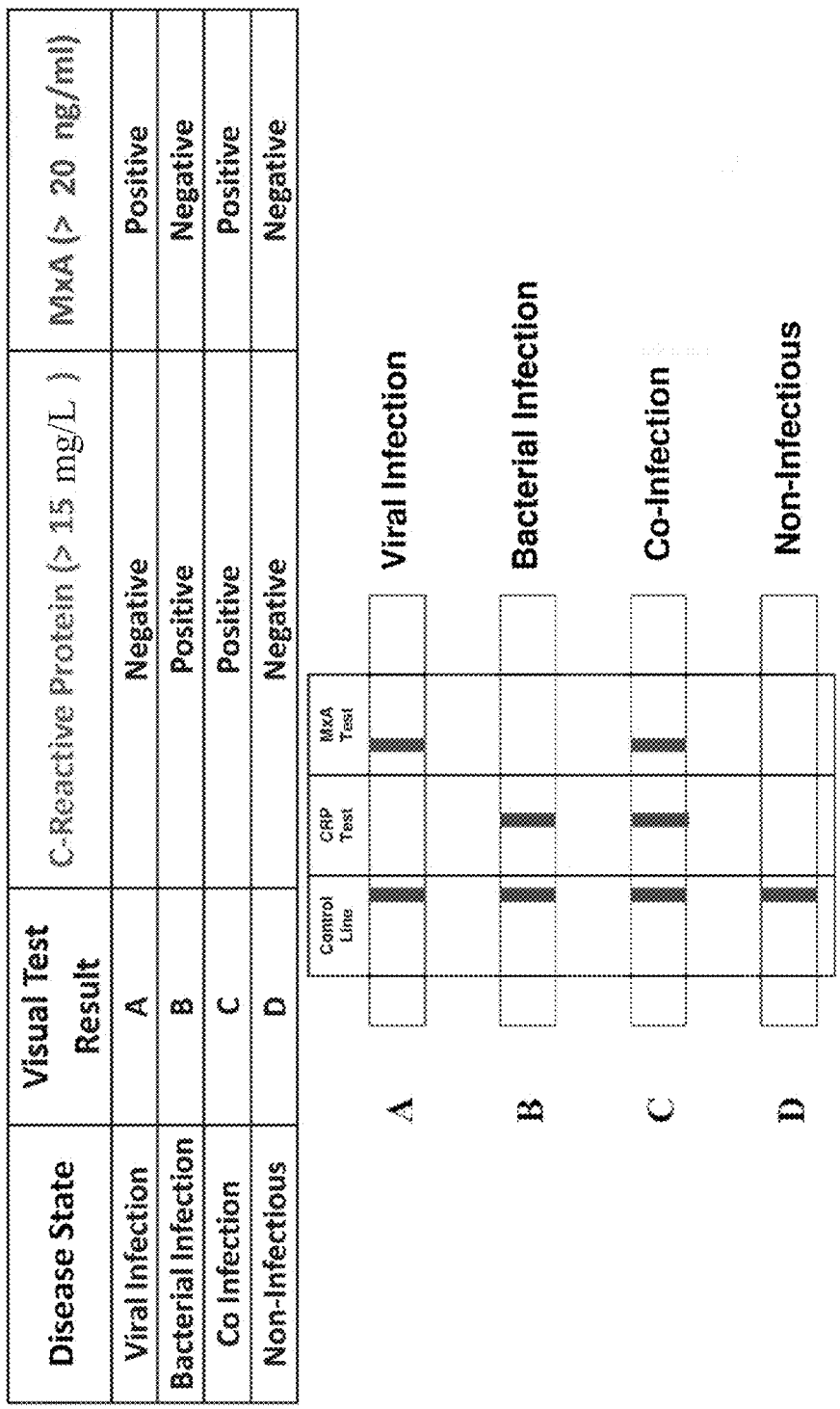
FIG. 1 shows rapid screening test window visual test results to distinguish viral and bacterial infections and an interpretation of those results.

The present invention provides a lateral flow assay that is capable of differentiating viral and bacterial infections. A combined point of care diagnostic device tests markers for both viral and bacterial infection and can effectively assist in the rapid differentiation of viral and bacterial infections, for example at the outpatient office or during an urgent care visit. This ability can dramatically reduce health care costs by limiting misdiagnosis and the subsequent overuse of antibiotics. Such a practice may limit antibiotic allergies, adverse events, and antibiotic resistance. The rapid result obtained from the test also permits a diagnosis while the patient is still being examined by the practitioner. In a preferred embodiment, the test result is obtained in under 10 minutes after applying the sample to the device, and it is preferably read at approximately 10 minutes. In samples that are highly positive, the test line is visible within approximately 1-5 minutes.

In a preferred embodiment of the present invention, the lateral flow immunoassay device of the present invention includes a sample-transporting liquid, which can be a buffer, and a chromatography test strip containing one or several fleece materials or membranes with capillary properties through which sample flows. Some preferred materials and membranes for the test strip include, but are not limited to, Polyethylene terephthalate (PET) fibers, such as Dacron® fibers, nitrocellulose, polyester, nylon, cellulose acetate, polypropylene, glass fibers, and combinations of these materials and their backings. In some embodiments of the invention, it is unnecessary to lyse the cells in the sample prior to applying it to the test strip.

One preferred method of the present invention uses a sample analysis device, for example a chromatography test strip, to determine if an infection is bacterial or viral. In this method, a sample is collected, and transferred to the chromatography test strip. In a preferred embodiment, the sample is a sample including leukocytes. The test strip includes a reagent zone. The reagent zone preferably includes at least one first reagent specific to a bacterial marker such that, when the bacterial marker present in the sample contacts the first reagent, a first labeled complex forms. The reagent zone also preferably includes at least one second reagent specific to a viral marker such that, when the viral marker present in the sample contacts the second reagent, a second labeled complex forms. A detection zone includes both a bacterial marker binding partner which binds to the first labeled complex and a viral marker binding partner which binds to the second labeled complex. The sample is then analyzed for the presence of the viral marker and/or the bacterial marker.

A preferred embodiment of a device of the present invention includes a sample application zone. The device also includes a reagent zone, which includes at least one first reagent specific to a bacterial marker such that, when a bacterial marker present in the sample contacts the first reagent, a first labeled complex forms and at least one second reagent specific to a viral marker such that, when a viral marker present in the sample contacts the second reagent, a second labeled complex forms. A detection zone on the device includes a bacterial marker binding partner which binds to the first labeled complex and a viral marker binding partner which binds to the second labeled complex. One example of a device that could be used is a chromatography test strip.

In a preferred embodiment, the presence of the viral marker or the bacterial marker is indicated by a test line visible to the naked eye. The presence of the viral marker may be indicated by a first test line while the presence of the bacterial marker is indicated by a second test line. In some embodiments, the first test line displays a first color when positive and the second test line displays a second color different from the first color when positive. In embodiments where both the first test line and the second test line are located in the same space on the sample analysis device, a third color is preferably formed when both the first test line and the second test line are positive. In other embodiments, the two test lines are spatially separate from each other on the device.

In one preferred embodiment, the bacterial marker is CRP. In another preferred embodiment, the viral marker is MxA.

In some preferred embodiments, the detection zone also includes a control line that is visible to the naked eye when the device is working.

In one preferred embodiment, the marker for viral infection is MxA and the marker for bacterial infection is C-reactive protein (CRP). High MxA protein levels are strongly correlated with systemic viral infection and increased CRP is more associated with bacterial infections. The present invention includes a rapid infectious screening test for identifying MxA and CRP in samples. MxA is present in leukocytes (white blood cells). Therefore, the sample can be taken anywhere leukocytes are available, for example in a peripheral blood sample, nasopharyngeal aspirates, tears, spinal fluid, and middle ear aspirates.

In some preferred embodiments, the threshold concentration of CRP in a sample needed to elicit a positive result is approximately 15 mg/L. In other preferred embodiments, the threshold concentration of MxA in a sample to elicit a positive result may be as low as approximately 15 ng/ml; however, the threshold concentration may by higher, in a range from approximately 20 ng/ml to approximately 250 ng/ml. The threshold concentration may depend on the size of the sample being applied to the test strip, as well as its dilution, if applicable.

In other embodiments, other markers for viral infection and/or bacterial infection may be used. For example, approximately 12% of host genes alter their expression after Lymphocytic Choriomeningitis Virus (LCMV) infection, and a subset of these genes can discriminate between virulent and nonvirulent LCMV infection. Major transcription changes have been given preliminary confirmation by quantitative PCR and protein studies and are potentially valuable candidates as biomarkers for arenavirus disease. Other markers for bacterial infection include, but are not limited to, procalcitonin, urinary trypsin inhibitor (uTi), lipopolysaccharide, IL-1, IL-6, IL-8, IL-10, ESR and an elevated WBC count (increased bands), Lactate, Troponin, vascular endothelial growth factor, platelet derived growth factor, cortisol, proadrenomedullin, macrophage migratory inhibitory marker, activated protein C, CD 4, 8, 13, 14, or 64, caspase, placenta derived growth factor, calcitonin gene-related peptide, high mobility group 1, copeptin, naturietic peptides, lipopolysaccharide binding protein, tumor necrosis factor alpha, circulating endothelial progenitor cells, complement 3a, and triggering receptor expressed on myeloid cells (trem-1).

In one embodiment, the infections being distinguished are respiratory infections. In other embodiments, other types of infections, which can be bacterial or viral, are differentiated using the system of the present invention. Some examples include, but are not limited to, encephalitis, meningitis, gastroenteritis, febrile respiratory illness (including bronchitis, pharyngitis, pneumonia), sinusitis, otitis media, urinary tract infections, and conjunctivitis.

Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

U.S. Published Patent Application No. 2007/0059682 discloses detecting an analyte and a sample which can also contain one or more interfering substances. This publication teaches separating the analyte from the interfering substances by capturing the interfering substances on the chromatographic carrier, and detecting the analyte on the carrier separated from the interfering substances.

U.S. Published Patent Application No. 2005/0175992 discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read out by the user. This enables point-of-care testing with results available during a patient visit. The inventions disclosed in this copending application are particularly advantageous for the diagnosis of conjunctivitis.

In a method of the invention, the sample to be analyzed is applied to a chromatographic carrier. The carrier can be made of one single chromatographic material, or preferably several capillary active materials made of the same or different materials and fixed on a carrier backing. These materials are in close contact with each other so as to form a transport path along which a liquid driven by capillary forces flows from an application zone, passing a reagent zone, towards one or more detection zones and optionally a waste zone at the other end of the carrier. In other embodiments, the liquid passes the reagent zone prior to flowing into the sample application zone. In an especially preferred embodiment, the carrier is a chromatographic test strip.

In some embodiments, the sample is directly applied to the carrier by dipping the carrier's application zone into the sample. Alternatively, application of the sample to the carrier may be carried out by collecting the sample with a dry or wetted wiping element from which the sample can be transferred, optionally after moistening, to the carrier's application zone. Usually, the wiping element is sterile and may be dry or pretreated with a fluid before the collection step. Materials suitable for wiping elements according to the invention may comprise synthetic materials, woven fabrics or fibrous webs. Some examples of such wiping elements are described in German Patents DE 44 39 429 and DE 196 22 503, which are hereby incorporated by reference.

Depending on the type of detection method, different reagents are present in the carrier's reagent zone, which, in some embodiments, is preferably located between the application zone and the detection zone or, in other embodiments, is preferably located before the application zone. In a sandwich immunoassay, it is preferred to have a labeled, non-immobilized reagent in the reagent zone that is specific to each bacterial and viral marker that is being detected. Thus, when a viral or bacterial marker present in the sample contacts the corresponding labeled viral or bacterial reagent present in the reagent zone, a labeled complex is formed between the marker and the corresponding labeled reagent. The labeled complex in turn is capable of forming a further complex with an immobilized viral or bacterial marker binding partner at a test line in the detection zone. In a competitive immunoassay, the reagent zone preferably contains a labeled, non-immobilized marker analogue which competes with the marker for the immobilized marker binding partner in the detection zone. The marker binding partners in the reagent zone and in the detection zone are preferably monoclonal, polyclonal or recombinant antibodies or fragments of antibodies capable of specific binding to the corresponding marker.

In a preferred embodiment, the present invention provides for the reduction of interfering substances that might be present in the sample to be tested. Since an interfering substance, e.g. a human anti-mouse antibody (HAMA), may also be capable of forming a complex with the labeled, non-immobilized reagent of the reagent zone and the immobilized binding partner of the detection zone, thus indicating a positive test result in the immunoassay, the carrier may further include at least one capturing zone. Each capturing zone contains an immobilized capturing reagent specifically binding to a certain interfering substance, thereby immobilizing the interfering substance in the capturing zone. As the capturing zone is separated from the detection zone by space, and the sample starts to migrate over the reagent zone and the capturing zone before reaching the carrier's detection zone, the method allows a separation of the interfering substance or substances from the analyte or analytes of interest. Preferably, the capturing zone is located between the reagent zone and the detection zone. However, the capturing zone may also be located between the application zone and the reagent zone.

Detection of the marker may be achieved in the detection zone. The binding molecule immobilizes the labeled complex or the labeled marker-analogue by immune reaction or other reaction in the detection zone, thus building up a visible test line in the detection zone during the process. Preferably, the label is an optically detectable label. Forming a complex at the test line concentrates and immobilizes the label and the test line becomes visible for the naked eye, indicating a positive test result. Particularly preferred are direct labels, and more particularly gold labels which can be best recognized by the naked eye. Additionally, an electronic read out device (e.g. on the basis of a photometrical, acoustic, impedimetrical, potentiometric and/or amperometric transducer) can be used to obtain more precise results and a semi-quantification of the analyte. Other labels may be latex, fluorophores or phosphorophores.

In one embodiment, the sensitivity of visually read lateral flow immunoassay tests is enhanced by adding a small quantity of fluorescing dye or fluorescing latex bead conjugates to the initial conjugate material. When the visible spectrum test line is visibly present, the test result is observed and recorded. However, in the case of weak positives that do not give rise to a distinct visual test line, a light of an appropriate spectrum, such as a UV spectrum, is cast on the test line to excite and fluorescent the fluorescing latex beads which are bound in the test line to enhance the visible color at the test line.

In a preferred embodiment, the reagents are configured such that the visible test line corresponding to the presence of the viral marker will be separate from the test line corresponding to the presence of the bacterial marker. Therefore, it can be readily determined whether the sample contained bacterial or viral markers (or both) simply by the location of the development of the test lines in the detection zone. In another preferred embodiment, the reagents may be chosen such that differently colored test lines are developed. That is, the presence of a viral marker will cause the development of a differently colored line than that developed by the presence of a bacterial marker. For example, the label corresponding to the reagent recognizing the viral marker may be red, whereas the label corresponding to the reagent recognizing the bacterial marker may be green. Differently colored labels that may be attached to the non-immobilized reagents are well known. Some examples include, but are not limited to, colloidal gold, colloidal selenium, colloidal carbon, latex beads, paramagnetic beads, fluorescent and chemiluminescent labels and mixtures thereof.

Figure 4A:
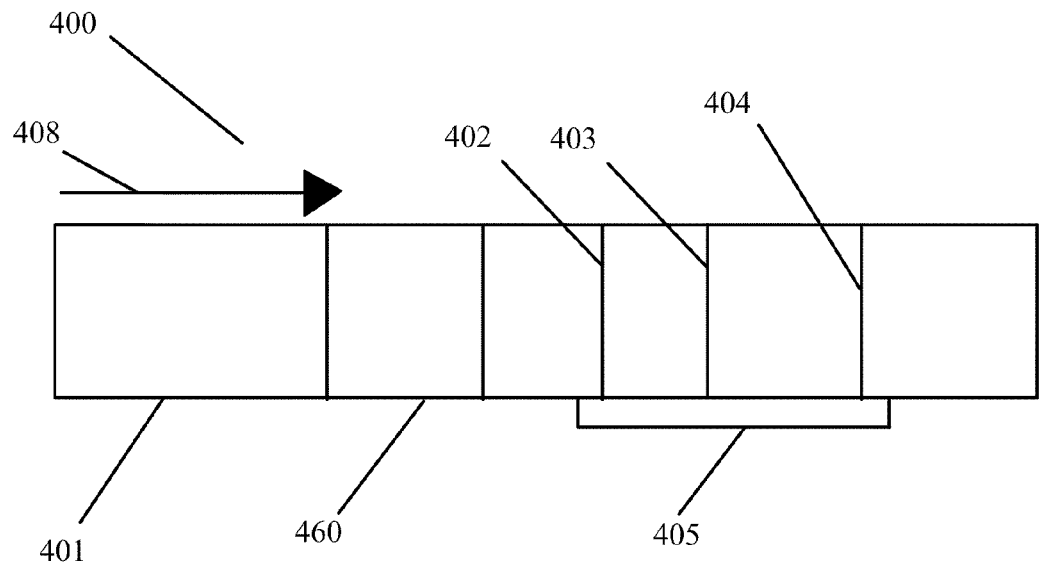
FIG. 4A shows a device with a test line corresponding to the presence of a viral marker and a second, separate test line that detects the presence of a bacterial marker in an embodiment of the present invention.
Figure 4B:
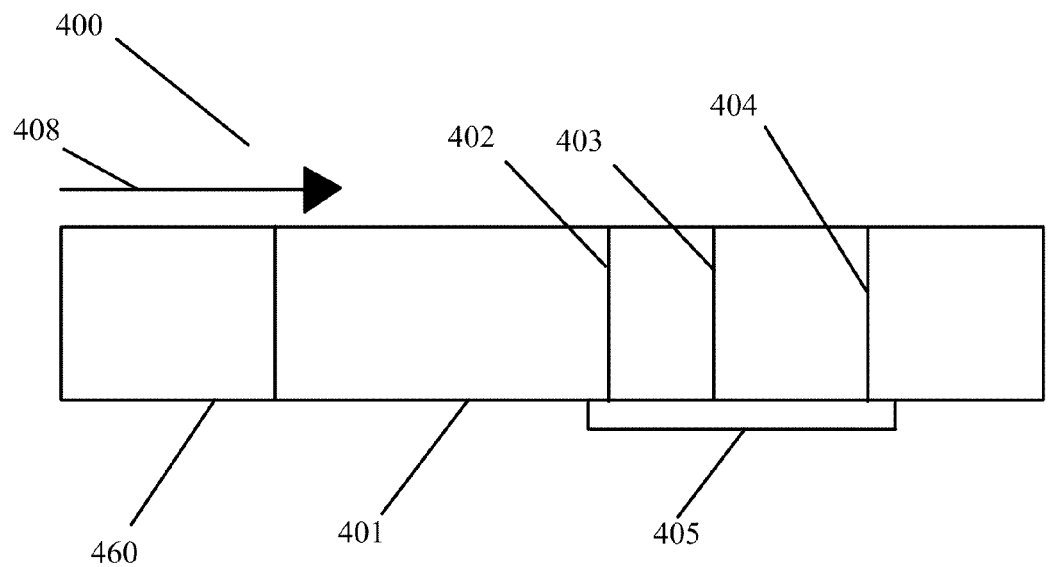
FIG. 4B shows a device with a test line corresponding to the presence of a viral marker and a second, separate test line that detects the presence of a bacterial marker in another embodiment of the present invention.

FIGS. 4A and 4B show a chromatography test strip (400) with a test line (402) corresponding to the presence of a viral marker and a second, separate test line (403) that detects the presence of a bacterial marker. The sample is applied to the application zone (401) of the chromatography test strip (400). As shown in FIG. 4A, the sample then passes a reagent zone (460) containing at least one labeled viral binding partner and at least one labeled bacterial binding partner that is eluted by and then able to migrate with a sample transport liquid (e.g. a buffer solution). Alternatively, as shown in FIG. 4B, the reagent zone (460) is located upstream of the sample application zone (401) such that the labeled binding partners in the reagent zone are eluted by the sample transport liquid and travel to the sample. The labeled viral binding partner is capable of specifically binding to a viral marker of interest to form a complex which in turn is capable of specifically binding to another specific reagent or binding partner in the detection zone. The labeled bacterial binding partner is capable of specifically binding to a bacterial marker of interest to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (400) in these embodiments.

The test strip (400) also includes a detection zone (405) containing at least one first section for detection of a viral marker, e.g. a test line (402), including an immobilized specific binding partner, complementary to the viral reagent complex formed by the viral marker and its labeled binding partner. Thus, at the test line (402), detection zone binding partners trap the labeled viral binding partners from the reagent zone (460) along with their bound viral markers. This localization of the viral marker with its labeled binding partners gives rise to an indication at the test line (402). At the test line (402), the presence of the viral marker is determined by qualitative and/or quantitative readout of the test line (402) indication resulting from the accumulation of labeled binding partners.

The detection zone (405) also includes at least one second section for detection of a bacterial marker, e.g. a test line (403), including an immobilized specific binding partner, complementary to the bacterial reagent complex formed by the bacterial marker and its labeled binding partner. Thus, at the test line (403), detection zone binding partners trap the labeled bacterial binding partners from the reagent zone (460) along with their bound bacterial markers. This localization of the bacterial marker with its labeled binding partners gives rise to an indication at the test line (403). At the test line (403), the presence of the bacterial marker is determined by qualitative and/or quantitative readout of the test line (403) indication resulting from the accumulation of labeled binding partners. While test line (402) is upstream of test line (403) relative to the direction of flow (408) in the figures, in alternative embodiments, test line (403) is upstream of test line (402). In still other embodiments, test lines (402) and (403) are located in the same location on the test strip.

Optionally, the detection zone (405) may contain further test lines to detect other viral and/or bacterial markers, as well as a control line (404). The control line (404) indicates that the labeled specific binding partner traveled through the length of the assay, even though it may not have bound any viral or bacterial markers, thus confirming proper operation of the assay. As shown in FIGS. 4A through 4B, the control zone (404) is preferably downstream of the test lines (402) and (403). However, in other embodiments, the control zone (404) may be located upstream of either or both of the test lines (402) and (403).

In a preferred embodiment, the control line (404) includes an antibody or other recombinant protein which binds to a component of the elution medium or other composition being used in the test. In embodiments where nucleic acids are the targets, the control line (404) preferably includes a nucleic acid complementary to the labeled nucleic acid being used as a binding partner for the target nucleic acid.

Although only one test line is shown in the figures for each of the viral and bacterial markers, multiple test lines for both or either of the viral and bacterial markers may be used within the spirit of the invention. In some embodiments where there are multiple bacterial and/or viral targets, the presence of each target preferably corresponds to a separate test line (402) or (403). In other embodiments, both the bacterial marker and the viral marker are detected on a single test line. In these embodiments, the presence of both a bacterial marker and a viral marker on the same test line has different characteristics than the presence of either a bacterial or viral marker alone. For example, the presence of both a bacterial marker and a viral marker on the same test line may be visually indicated by a different color than the presence of either a bacterial marker or a viral marker alone.

Fresh whole blood samples of patients showing symptoms of viral infections (flu like symptoms and fever of >100.5° F.)) were tested to determine what levels of MxA in the blood could be detected with the lateral flow tests described herein. The lateral flow assays used in these experiments had a similar configuration as the device shown in FIG. 4B described above, without a second test line for the presence of a bacterial marker. More specifically, the test strip included a reagent zone upstream of a sample application zone. The reagent zone included mobilizable antibodies to MxA (Kyowa Hakko Kirin Co., Ltd., Tokyo, Japan) labeled with colloidal gold. The test strip also included a test line in a detection zone. The test line included an immobilized antibody for MxA (Kyowa Hakko Kirin Co., Ltd., Tokyo, Japan). The control line in the detection zone included rabbit anti-chicken antibody plus rabbit Ig (for an extra stabilizing effect), which binds to mobilized chicken IgY labeled with blue latex beads.

The whole blood samples were collected with EDTA as the anticoagulant. In these tests, the amount of MxA protein in the blood samples was determined using an MxA Protein ELISA Test kit (Kyowa Hakko Kirin Co., Ltd., Tokyo, Japan). The blood was lysed 1:10 with lysing solution provided in the kit, prior to being applied to the test strip. 100 µl of lysed blood was tested in the ELISA test. 10 µl of lysed blood was used as the sample in the MxA lateral flow test.

The lysed blood samples were applied to the application zone of the test strip. The labeled MxA antibodies in the reagent zone were eluted by the sample transport liquid and traveled to the blood samples. At the test line, the immobilized MxA antibody trapped any labeled MxA antibody from the reagent zone bound to MxA. This localization of the MxA with its labeled antibody gave rise to a red visual indication at the test line if there was a sufficient concentration of MxA.

TABLE 1

| Calibrator Concentration (ng/ml) | OD | Lateral Flow MxA Test |
|---|---|---|
| 24 | 2.223 | + |
| 12 | 1.259 | Shadow |
| 6 | 0.700 | Not tested |
| 3 | 0.391 | Not tested |
| 1.5 | 0.220 | Not tested |
| .75 | 0.140 | Not tested |
| 0.38 | 0.102 | Not tested |

Table 1 shows the MxA ELISA kit standards run per the test instructions. As shown in Table 1, an MxA concentration of 24 ng/ml produced a positive result in the lateral flow test. The kit standard was used to generate the standard curve from which the MxA concentrations were determined.

Table 2 shows the results of clinical fresh whole blood samples of patients showing symptoms of viral infections (flu like symptoms and fever of >100.5° F.)).

TABLE 2

| Sample | OD | Concentration (ng/ml) | Concentration × dilution (10×) (ng/ml) | Lateral Flow MxA Test |
|---|---|---|---|---|
| A | 0.008 | 0 | 0 | − |
| B | 0.123 | 0.591 | 5.911 | − |
| C | 1.125 | 10.489 | 104.894 | + |
| D | 0.111 | 0.487 | 4.872 | − |
| E | 0.068 | 0.121 | 1.211 | − |
| F | 0.300 | 2.177 | 21.77 | + |
| G | 0.027 | 0 | 0 | − |

The OD (optical density) values were used in combination with the standard curve from the kit's standard in order to determine the MxA concentration in the samples. The concentration (ng/ml) column was the concentration as diluted with the lysing agent. The concentration×dilution (10×) (ng/ml) column was the actual concentration in the whole blood sample. As shown in the table, the lateral flow test produced a positive result for MxA in samples C and F, which had approximately 105 ng/ml of MxA and approximately 22 ng/ml of MxA, respectively, in the samples.

Table 3 shows the results of frozen whole blood samples from normal individuals from the Tennessee blood bank. None of the blood samples had any discernible amounts of MxA, and all of them were negative in the lateral flow test.

TABLE 3

| Sample | OD | CONCENTRATION (ng/ml) | CONCENTRATION × DILUTION (10×) (ng/ml) | Lateral Flow MxA Test |
|---|---|---|---|---|
| 1 | 0.003 | 0 | 0 | − |
| 2 | 0.014 | 0 | 0 | − |
| 3 | 0.008 | 0 | 0 | − |
| 4 | 0.035 | 0 | 0 | − |
| 5 | 0.011 | 0 | 0 | − |
| 6 | 0.007 | 0 | 0 | − |
| 7 | (0.017) | 0 | 0 | − |
| 8 | (0.006) | 0 | 0 | − |
| 9 | 0.028 | 0 | 0 | − |
| 10 | 0.012 | 0 | 0 | − |
| 11 | 0.028 | 0 | 0 | − |

TABLE 3-continued

| Sample | OD | CONCENTRATION (ng/ml) | CONCENTRATION × DILUTION (10×) (ng/ml) | Lateral Flow MxA Test |
|---|---|---|---|---|
| 12 | 0.02 | 0 | 0 | − |
| 13 | 0.044 | 0 | 0 | − |
| 14 | 0.023 | 0 | 0 | − |
| 15 | 0.032 | 0 | 0 | − |
| 16 | 0.02 | 0 | 0 | − |
| 17 | 0.032 | 0 | 0 | − |
| 18 | 0.009 | 0 | 0 | − |
| 19 | 0.035 | 0 | 0 | − |
| 20 | 0.022 | 0 | 0 | − |
| 21 | 0.017 | 0 | 0 | − |
| 22 | 0.188 | 1.163 | 11.631 | − |
| 23 | 0.014 | 0 | 0 | − |
| 24 | 0.005 | 0 | 0 | − |
| 25 | 0.039 | 0 | 0 | − |

Table 4 shows freshly frozen whole blood samples from BioReclamation (BioReclamation, Hicksville, N.Y.) of patients showing symptoms of viral infections (flu like symptoms and fever of >100.5° F.)). None of these patients had ODs that corresponded to MxA levels higher than approximately 8 ng/ml. These samples were all negative in the lateral flow test.

TABLE 4

| Sample | OD | Concentration (ng/ml) | Concentration × dilution (10×) (ng/ml) | Lateral Flow MxA Test |
|---|---|---|---|---|
| 26 | 0.029 | 0 | 0 | − |
| 27 | 0.026 | 0 | 0 | − |
| 28 | 0.018 | 0 | 0 | − |
| 29 | 0.146 | 0.792 | 7.92 | − |
| 30 | 0.004 | 0 | 0 | − |
| 31 | 0.128 | 0.635 | 6.35 | − |

The results of these tests indicate that the lateral flow tests described herein can detect MxA levels at least as low as approximately 20 ng/ml in a 10 µl sample (diluted 1:10).

One example of a rapid screening test for distinguishing viral and bacterial infection is shown in FIG. 1. As discussed above, MxA is a diagnostic marker for viral infection, while CRP is a diagnostic marker for bacterial infection. In this example, a blue line ("control line" in A-D of the Figure) represents the control. A green line represents a C-reactive protein (CRP) level >15 mg/L ("CRP test" in A-D of the figure). A red line represents an MxA level >20 ng/ml ("MxA test" in A-D of the figure). A positive result for the MxA protein, with a negative result for the CRP protein indicates only a viral infection (Visual Test Result A). A positive result for the (CRP) with a negative result for the MxA protein indicates only a bacterial infection (Visual Test Result B). A positive result for both MxA and CRP indicates co-infection (infection with both a bacteria and a virus) (Visual Test Result C). No bacterial or viral infection is indicated by a negative result for both MxA and CRP (Visual Test Result D). While particular color lines are discussed in this example, other colors, or the same colors at different locations on the test strip to indicate viral or bacterial markers, are within the spirit of the present invention.

When development of different colored lines is utilized, the lines may or may not be separated by space. In the latter instance, the labels are chosen such that the color seen when both markers are present is different from the colors seen when the individual markers are present. For example, the presence of the viral marker may be indicated by a red line; the presence of the bacterial marker by a blue line; and the presence of both by a purple line (combined red and blue).

Figure 2:
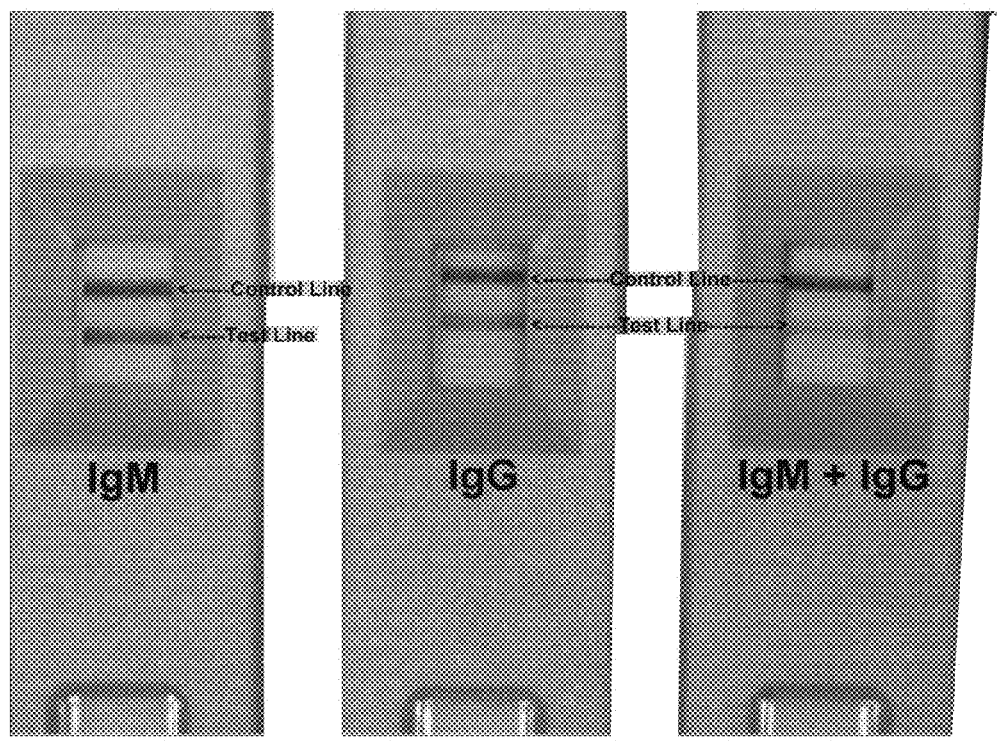
FIG. 2 shows three cassettes with different colored test lines.

The use of two colors to distinguish acute and chronic infection is shown in FIG. 2. In the first cassette, only IgM antibodies are present, which indicates an acute infection. In this cassette, the test line is red. In the second cassette, the test line is blue because the immunoglobulins are IgG. The third cassette shows an intermediate case, where both IgM and IgG antibodies are present. Consequently, the test line is purple. While this example is shown to test for IgMs and IgGs, the same concept is alternatively used with a single line which detects both viral and bacterial markers for infection.

In another preferred embodiment, the test strip may also include a control section which indicates the functionality of the test strip. FIG. 1 shows a control line. FIG. 2 shows an example where there is a control section for all three cassettes. If present, the control section can be designed to convey a signal to the user that the device has worked. For example, the control section may contain a reagent (e.g., an antibody) that will bind to the labeled reagents from the reagent zone. For example, an anti-mouse antibody may be used if the labeled antibody is of murine origin, to confirm that the sample has permeated the test strip. Alternatively, the control section may contain an anhydrous reagent that, when moistened, produces a color change or color formation, e.g. anhydrous copper sulphate which will turn blue when moistened by an aqueous sample. As a further alternative, the control section could contain immobilized viral and bacterial markers which will react with excess labeled reagent from the reagent zone. The control section may be located upstream or downstream from the detection zone. A positive control indicator tells the user that the sample has permeated the required distance through the test device.

Figure 3:
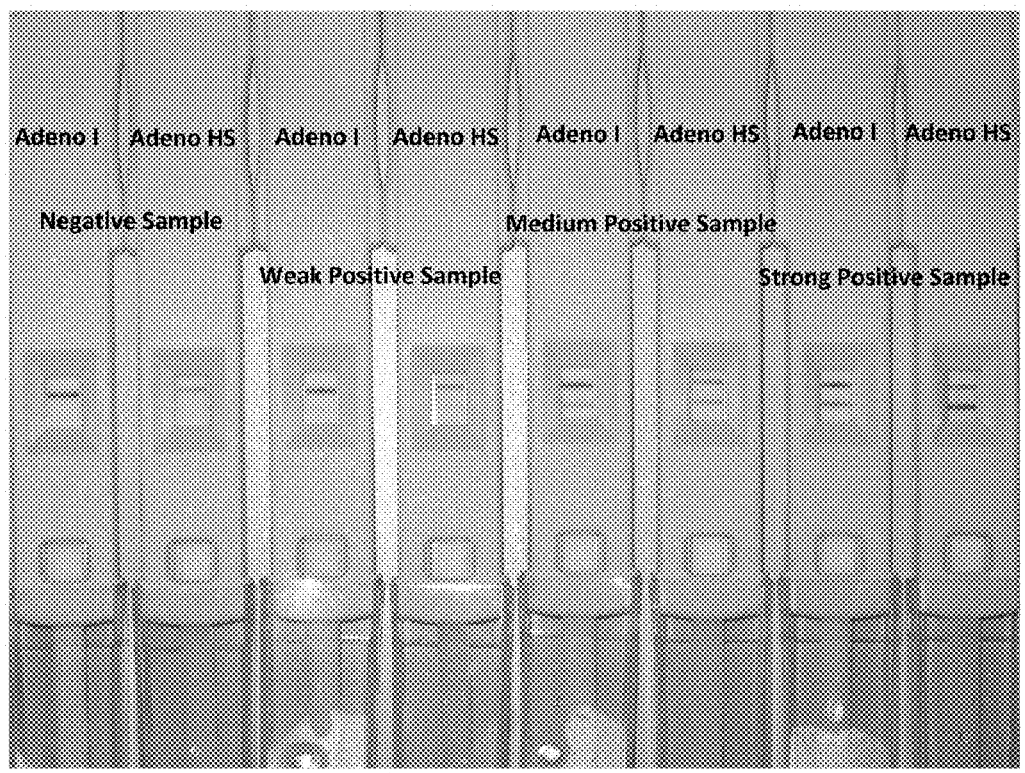
FIG. 3 shows a comparison of a two line detector, where both lines are the same color, and an extra sensitive two line detector, where the two lines are different colors.

FIG. 3 compares two test strips, the "Adeno 1" and the "Adeno HS", which both include control lines. In the Adeno 1, both the control (upper line on each cassette) and test (lower line on each cassette) lines are red. In the Adeno HS, the control line is blue and the test line is red. In embodiments where the control line is a different color than the test line, it is easier to distinguish between the two lines, and to ensure that the test is working.

In some preferred embodiments, the devices and methods of the present invention include a lysis zone to help differentiate viral and bacterial infections. In these embodiments, the sample that has been collected is not lysed prior to collection and transfer to the sample analysis device. This decreases the number of steps needed to collect and prepare the sample for analysis. One situation where a lysis agent improves assay efficiency is in assaying for the presence of MxA. As discussed herein, the presence of this protein can help to distinguish between bacterial and viral infection in febrile children. In situ lysis using a combination of 1% to 6% weight/volume CHAPS and 0.5% to 2% weight/volume NP40 as the lysis agent improves detection of MxA in fresh or frozen whole blood.

In the embodiments utilizing a lysis agent, following sample loading, the sample traveling with the transport liquid (buffer) will encounter the lysis agent. The lysis agent will have preferably been pre-loaded onto the test strip and is eluted by the transport liquid. In some preferred embodiments the lysis agent has been dried into the test strip. Alternatively, the lysis agent may be pre-dried by freeze drying or lyophilizing and then pre-loaded into the test strip. In other embodiments, the lysis agent may be absorbed, adsorbed, embedded or trapped on the test strip. The initially dried lysis agent is preferably localized between the sample application zone and a reagent zone. In embodiments where the reagent zone is upstream of the sample application zone, the lysis zone is downstream of the sample application zone. The lysing agent is preferably soluble in the sample transport liquid, and the lysing agent is solubilized and activated upon contact with the sample transport liquid. The sample transport liquid then contains both lysing agent in solution or suspension and sample components in suspension. Any lysis-susceptible components in a sample, then being exposed in suspension to the lysing agent, are themselves lysed in situ. The running buffer then carries the analyte, including any lysis-freed components, to the detection zone.

The location where the lysis agent is pre-loaded and dried can be varied as needed. In order to maximize the time that the sample has to interact with the lysis agent as well as to minimize the amount of lysis agent reaching the detection zone, the dried, absorbed, adsorbed, embedded, or trapped lysis agent may be located in or just downstream of the sample application zone. Or, in order to minimize the distance along which the lysis product must travel before reaching the reagent zone, the dried lysis agent may be located closer to the reagent zone. In other embodiments, the lysis agent may be included in the running buffer.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

Selection of a specific lysing environment and agent will depend on the viral and bacterial markers and the assay. The pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets.

As to ionic strength established by the lysis agent, both the high and low ionic strength may be used to lyse. For example, a lower ionic strength (hypotonic) tends to break up erythrocytes. For example, water by itself can lyse erythrocytes. Higher ionic strength environments may be used to rupture certain cell walls and membranes.

As to specific lysis agents, they may be grouped and selected based on their properties: salts, amphoteric and cationic agents, ionic and non-ionic detergents. The salt, Ammonium Chloride ($NH_4Cl$), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, SDS, Cholate, and Deoxycholate. Ionic detergents are good solubilizing agents. Antibodies retain their activity in 0.1% SDS or less. Common non-ionic detergents include, but are not limited to, Octylglucoside, Digitonin, C12E8, Lubrol, Triton X-100, Noniodet P-40, Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

Surfactants are generally wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

The lysis agent itself should not interfere with any other assay detector or indicator agents and thus does not interfere with any other assay interactions and reactions to such an extent as to prevent practical operation of the assay. A lysis agent should have sufficient shelf life to allow manufacture, distribution and storage before use of a test strip in point-of-care testing.

In preferred embodiments where MxA is the viral marker, in situ lysis using a combination of 1% to 6% weight/volume CHAPS and 0.5% to 2% weight/volume NP40 as the lysis agent is preferably used. As a more specific example, 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume) are dried onto a lysis zone of a test strip.

In a preferred embodiment, as shown in FIGS. 5A through 5D, the sample is applied to the application zone (201) on a chromatography test strip (200). The sample passes a lysis zone (250), where a lysis agent will have preferably been pre-loaded onto the test strip and is eluted by the transport liquid. The lysis agent lyses any lysis-susceptible components in the sample in situ.

The chromatographic test strip contains a sample application zone (201), a lysis zone (250) containing a lysis agent, and a reagent zone (260) containing at least one labeled binding partner that binds to a viral marker and at least one labeled binding partner that binds to a bacterial marker that are eluted by and then able to migrate with a sample transport liquid (e.g. a buffer solution). While the reagent zone (260) is shown downstream of the sample application zone in these figures, in alternative embodiments, the reagent zone (260) could be upstream of the sample application zone (see FIG. 4B), as long as the reagents encounter the sample at some point after the sample reaches the lysis zone and is effectively lysed. The labeled binding partners are capable of specifically binding to a viral or bacterial marker of interest to form a complex which in turn is capable of specifically binding to another specific reagent or binding partner in the detection zone. Although not shown in these Figures, an absorbent pad, as well as other known lateral flow immunoassay components including, but not limited to, a waste zone, a carrier backing, a housing, and an opening in the housing for result read out, may optionally also be a component of the test strip (200) in these embodiments.

In a preferred embodiment, the lysis agent is localized in the lysis zone (250) between the sample application zone (201) and the reagent zone (260). The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the sample, including any lysis-freed components, to the detection zone (205).

Figure 5A:
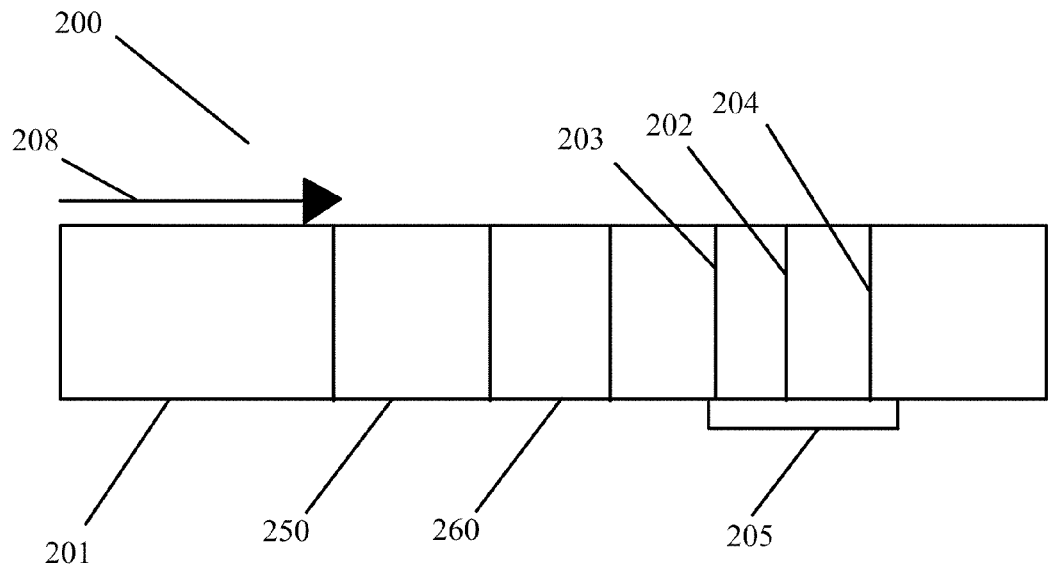
FIG. 5A shows a sample analysis device including a lysis zone located between a sample application zone and a reagent zone in an embodiment of the present invention.
Figure 5B:
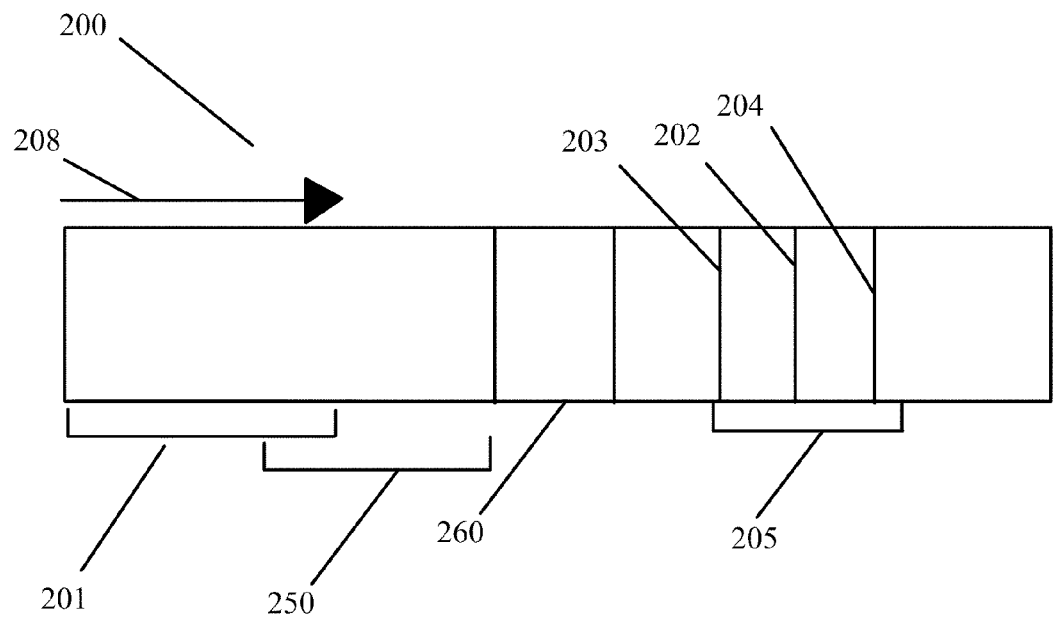
FIG. 5B shows a sample analysis device including a lysis zone overlapping a sample application zone in an embodiment of the present invention.
Figure 5C:
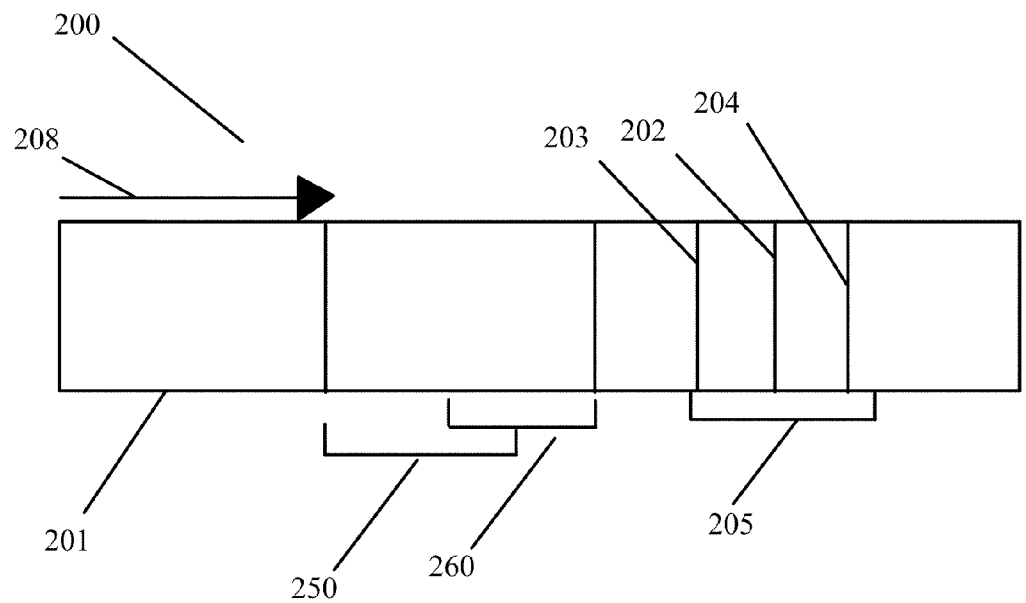
FIG. 5C shows a sample analysis device including a lysis zone overlapping a reagent zone in an embodiment of the present invention.
Figure 5D:
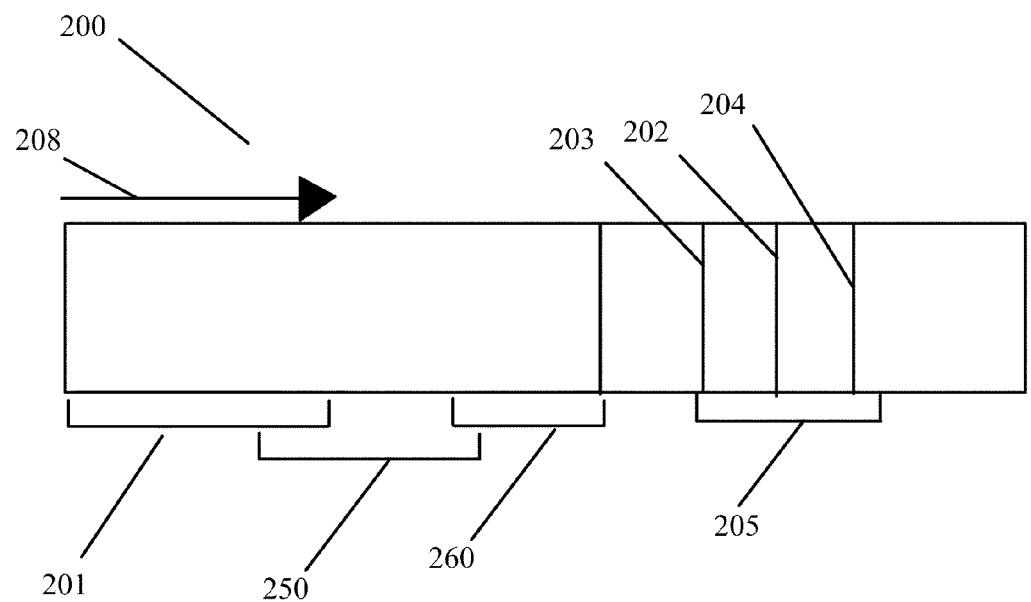
FIG. 5D shows a sample analysis device including a lysis zone overlapping a sample application zone and a reagent zone in an embodiment of the present invention.

The lysis zone (250) is preferably located between the sample application zone (201) and the reagent zone (260), as shown in FIG. 5A. In other embodiments, the lysis zone (250) overlaps the sample application zone (201), the reagent zone (260) or both the sample application zone (201) and the reagent zone (260) as shown in FIGS. 5B, 5C, and 5D, respectively. Note that the figures are schematic, and are not drawn to scale. The amount of overlap between the different zones (as shown in FIGS. 5B through 5D) may be highly variable.

The test strip (200) also includes a detection zone (205) containing a first section for detection of at least one bacterial marker, e.g. a test line (203), including an immobilized specific binding partner, complementary to the bacterial conjugate formed by the bacterial marker and its labeled binding partner. Thus, at the test line (203), detection zone binding partners trap the bacterial labeled binding partners from the reagent zone (260) along with their bound bacterial markers. This localization of the bacterial markers with their labeled binding partners gives rise to an indication at the test line (203). At the test line (203), the presence of a bacterial marker is determined by qualitative and/or quantitative readout of the test line (203) indication resulting from the accumulation of labeled binding partners.

The detection zone (205) also includes a second section for detection of at least one viral marker, e.g. a test line (202), including an immobilized specific binding partner, complementary to the viral conjugate formed by the viral marker and its labeled binding partner. Thus, at the test line (202), detection zone binding partners trap the viral labeled binding partners from the reagent zone (260) along with their bound viral markers. This localization of the viral markers with their labeled binding partners gives rise to an indication at the test line (202). At the test line (202), the presence of a viral marker is determined by qualitative and/or quantitative readout of the test line (202) indication resulting from the accumulation of labeled binding partners. While test line (203) is upstream of test line (202) relative to the direction of flow (208) in the figures, in alternative embodiments, test line (202) is upstream of test line (203). In still other embodiments, test lines (202) and (203) are located in the same location on the test strip.

Optionally, the detection zone (205) may contain further test lines to detect other bacterial and/or viral markers, as well as a control line (204). The control line (204) indicates that the labeled specific binding partner traveled through the length of the assay, even though it may not have bound any markers, thus confirming proper operation of the assay. As shown in FIGS. 5A through 5D, the control zone (204) is preferably downstream of the test lines (203) and (202). However, in other embodiments, the control zone (204) may be located upstream of either or both of the test lines (203) and (202).

In a preferred embodiment, the control line (204) includes an antibody or other recombinant protein which binds to a component of the elution medium or other composition being used in the test. In embodiments where nucleic acids are the targets, the control line (204) preferably includes a nucleic acid complementary to the labeled nucleic acid being used as a binding partner for the target nucleic acid.

Although only one test line is shown in the figures, multiple test lines are within the spirit of the invention. In some embodiments where there are multiple targets, the presence of each target preferably corresponds to a separate test line (202). In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone.

In other embodiments, it is possible to have one or more mild lysis agents in the running buffer itself. In these embodiments, there is no adverse effect on the reagent zone which will be downstream and the sample can either be upstream or downstream of the reagent zone. A lysing enzyme in the running buffer can "target" its substrate and cut it to open up the cell membrane or cell wall. As an example, penicillin can excise or "punch a hole" in a susceptible bacteria. In other embodiments, when the lysis agent is applied to the sample collection material, then the reagent zone may be upstream of the sample application zone.

As an example, one or more lysis agents are dried onto the sample application zone of a lateral flow strip. On a per strip basis, the lysis agent is made of approximately 2 microliters of 100 mM HEPES buffer (pH 8.0) containing 5% CHAPS and 2% NP-40 with 150 mM Sodium Chloride, 0.1% BSA, and 0.1% Sodium Azide (all percentages weight/volume). Up to 10 microliters of whole blood are then added to the sample application zone to be lysed in situ. MxA protein is released from inside white blood cells to react with an MxA monoclonal antibody on a visual tag (colloidal gold or visible latex beads). This complex traverses with a running buffer containing Triton X-100 and is captured by MxA monoclonal antibodies immobilized at the test line of the nitrocellulose membrane. This binding at the test line gives rise to a visible indication.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for determining if an infection is bacterial and/or viral, comprising the steps of:
   a) collecting a sample;
   b) transferring the sample to a sample analysis device comprising:
      a reagent zone comprising:
         at least one first reagent specific to CRP such that, when CRP present in the sample contacts the first reagent, a first labeled complex forms; and
         at least one second reagent specific to MxA such that, when MxA present in the sample contacts the second reagent, a second labeled complex forms;

a detection zone comprising a first binding partner which binds to the first labeled complex and a second binding partner which binds to the second labeled complex; and a lysis zone comprising at least one lysis agent comprising approximately 1% to 6% weight/volume CHAPS and approximately 0.5% to 2% weight/volume NP40;

c) lysing the sample on the sample analysis device; and d) analyzing the sample for a presence of CRP and/or MxA.

2. The method of claim 1, wherein step d) comprises the substeps of:

i) eluting the sample on the sample analysis device; and ii) visually determining a result from the detection zone.

3. The method of claim 1, wherein a threshold concentration of CRP in a sample that elicits a positive result is at least approximately 15 mg/L.

4. The method of claim 1, wherein a threshold concentration of MxA in a sample that elicits a positive result is at least approximately 15 ng/ml.

5. The method of claim 1, wherein the lysis agent comprises 100 mM HEPES buffer (pH 8.0) including 5% CHAPS and 2% NP-40 with 150 mM Sodium Chloride, 0.1% BSA, and 0.1% Sodium Azide.

6. The method of claim 1, wherein the sample comprises a plurality of leukocytes.

7. The method of claim 6, wherein step c) lyses the leukocytes.

8. The method of claim 1, wherein the sample analysis device is a lateral flow chromatography test strip.

9. The method of claim 1, wherein the sample is a sample of whole blood.

10. The method of claim 1, wherein the presence of MxA or CRP is indicated by test lines located in the detection zone visible to the naked eye.

11. The method of claim 10, wherein the presence of MxA is indicated by a first test line located in the detection zone and the presence of CRP is indicated by a second test line located in the detection zone.

12. The method of claim 11, wherein the first test line displays a first color when positive and the second test line displays a second color different from the first color when positive.

13. The method of claim 12, wherein both the first test line and the second test line are located in the same space on the sample analysis device such that a third color is formed when both the first test line and the second test line are positive.

14. The method of claim 11, wherein the first test line is spatially separate from the second test line on the sample analysis device.

15. The method of claim 1, wherein the sample is a blood sample.

16. The method of claim 1, wherein the sample comprises leukocytes.

17. The method of claim 1, wherein the sample is taken from a location selected from the group consisting of: peripheral blood, nasopharyngeal aspirates, tears, spinal fluid, and middle ear aspirates.

* * * * *